United States Patent
Shi et al.

(10) Patent No.: US 10,271,843 B2
(45) Date of Patent: Apr. 30, 2019

(54) SURGICAL INSTRUMENT WITH LOCKOUT MECHANISM

(71) Applicant: Covidien LP, Mansfield, MA (US)

(72) Inventors: Stone Shi, Jiangsu Province (CN); Qianhong Yang, Pudong Shanghai (CN); Shunhong Xu, Shanghai (CN)

(73) Assignee: Covidien LP, Mansfield, MA (US)

( * ) Notice: Subject to any disclaimer, the term of this patent is extended or adjusted under 35 U.S.C. 154(b) by 519 days.

(21) Appl. No.: 14/888,162

(22) PCT Filed: Jun. 17, 2013

(86) PCT No.: PCT/CN2013/077331
§ 371 (c)(1),
(2) Date: Oct. 30, 2015

(87) PCT Pub. No.: WO2014/201608
PCT Pub. Date: Dec. 24, 2014

(65) Prior Publication Data
US 2016/0106418 A1    Apr. 21, 2016

(51) Int. Cl.
*A61B 17/04*    (2006.01)
*A61B 17/10*    (2006.01)
(Continued)

(52) U.S. Cl.
CPC ........ *A61B 17/068* (2013.01); *A61B 17/1155* (2013.01); *A61B 2017/00367* (2013.01);
(Continued)

(58) Field of Classification Search
CPC ............ A61B 17/068; A61B 17/07207; A61B 2017/00367
(Continued)

(56) References Cited

U.S. PATENT DOCUMENTS 3,193,165 A    7/1965    Akhalaya et al.
3,388,847 A    6/1968    Kasulin et al.
(Continued)

FOREIGN PATENT DOCUMENTS

CA    908529 A    8/1972
CN    101507629    8/2009
(Continued)

OTHER PUBLICATIONS

Supplementary European Search Report dated May 9, 2017 issued in corresponding EP Application No. 13887355.9.
(Continued)

*Primary Examiner* — Robert Long

(57) ABSTRACT

A surgical instrument comprising a handle assembly, an elongated portion, a head portion, an approximation mechanism, and a lockout mechanism is disclosed. The handle assembly comprises a movable handle and a stationary handle. The elongated portion extends distally from the handle assembly and defines a longitudinal axis. The head portion is disposed adjacent a distal portion of the elongated portion, and comprises a first jaw member and a second jaw member. The approximation mechanism comprises a drive member disposed in mechanical cooperation with the first jaw member and is configured to longitudinally move the first jaw member in relation to the second jaw member. The lockout mechanism is configured to selectively permit actuation of the movable handle to eject fasteners from the second jaw member. The lockout mechanism comprises a pin extending from the movable handle and is slidingly engaged with a slot in the drive member.

11 Claims, 17 Drawing Sheets

(51) Int. Cl.
*A61B 17/068* (2006.01)
*A61B 17/115* (2006.01)
*A61B 17/00* (2006.01)
*A61B 90/00* (2016.01)

(52) U.S. Cl.
CPC .............. *A61B 2017/00526* (2013.01); *A61B 2090/0811* (2016.02)

(58) Field of Classification Search
USPC .......................................... 227/175.1–182.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,383,634 A * | 5/1983 | Green ................. A61B 17/072 227/135 |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |

(56) References Cited

U.S. PATENT DOCUMENTS

| | | |
|---|---|---|
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |

(56) References Cited

U.S. PATENT DOCUMENTS

| | | |
|---|---|---|
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2005/0023325 A1 | 2/2005 | Gresham et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1* | 9/2009 | Milliman ........... A61B 17/0686 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0051669 A1 | 3/2010 | Milliman |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0213240 A1* | 8/2010 | Kostrzewski ........ A61B 17/072 227/180.1 |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0006102 A1* | 1/2011 | Kostrzewski ........ A61B 17/115 227/176.1 |
| 2011/0011916 A1 | 1/2011 | Levine |
| 2011/0017800 A1* | 1/2011 | Viola .................. A61B 17/115 227/175.1 |
| 2011/0114697 A1 | 5/2011 | Baxter, III et al. |
| 2011/0114700 A1 | 5/2011 | Baxter, III et al. |

(56) References Cited

U.S. PATENT DOCUMENTS

| | | |
|---|---|---|
| 2011/0139852 A1* | 6/2011 | Zingman .............. A61B 17/072 227/176.1 |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0272448 A1* | 11/2011 | Scirica ............. A61B 17/07207 227/175.2 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0263547 A1* | 9/2014 | Tanner ............... A61B 17/1155 227/175.2 |
| 2015/0351769 A1* | 12/2015 | Lee .................... A61B 17/1155 227/179.1 |
| 2018/0296219 A1* | 10/2018 | Zhang .................. A61B 90/00 |

FOREIGN PATENT DOCUMENTS

| | | |
|---|---|---|
| CN | 103120599 | 5/2013 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2272443 | 1/2011 |
| EP | 2524656 A2 | 11/2012 |
| EP | 2790592 A1 | 10/2014 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |
| WO | 2013090221 A1 | 6/2013 |

OTHER PUBLICATIONS

Chinese Office Action dated Jun. 29, 2017 issued in corresponding Chinese Application No. 2013800774913.
Australian Office Action dated Feb. 23, 2018 issued in corresponding Australian Application No. 2013393223.
European Search Report dated Jan. 30, 2017 issued in corresponding EP Application No. 13887355.9.
International Search Report for (PCT/CN2013/077331) dated Feb. 28, 2014 (3 pages).

* cited by examiner

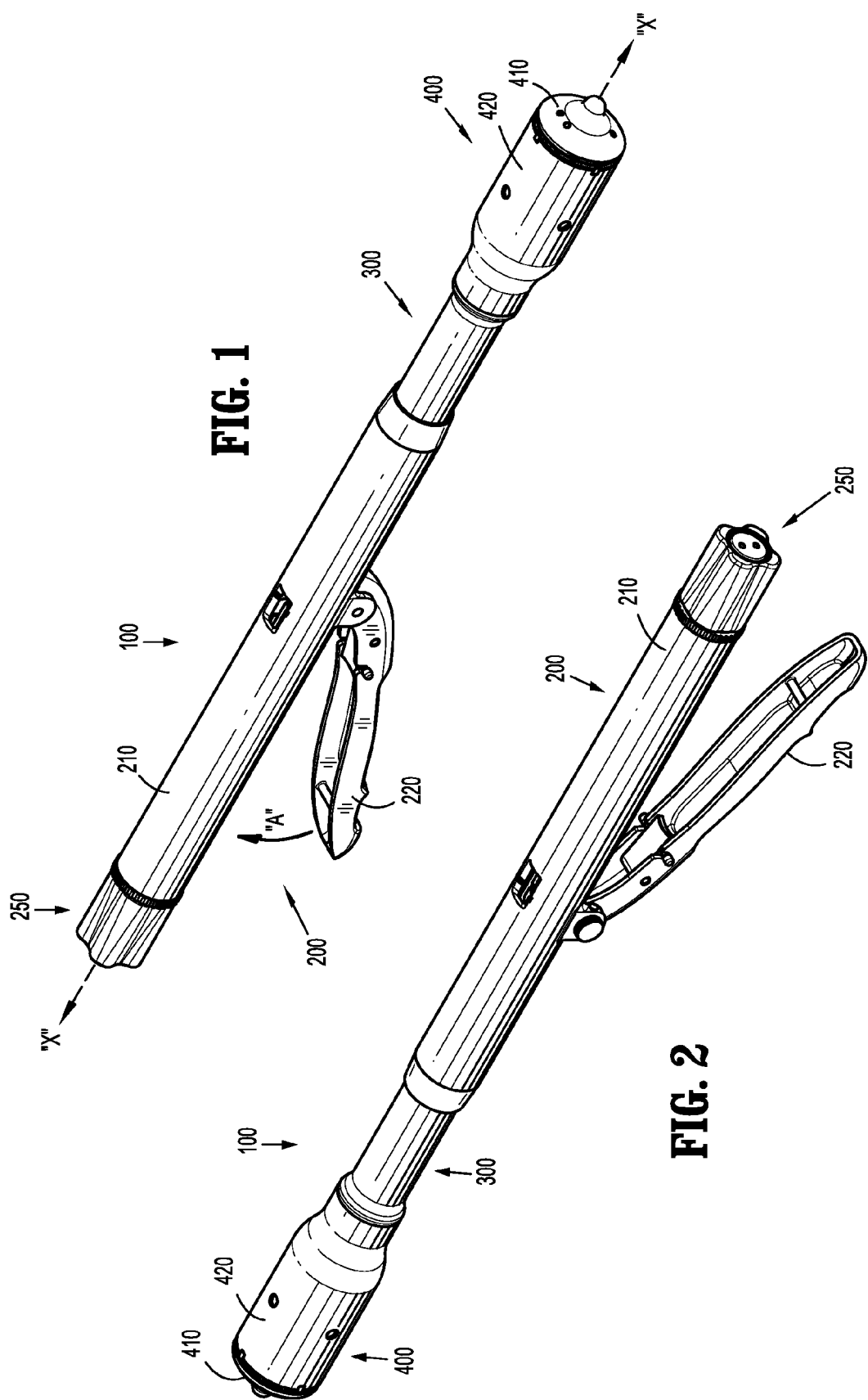

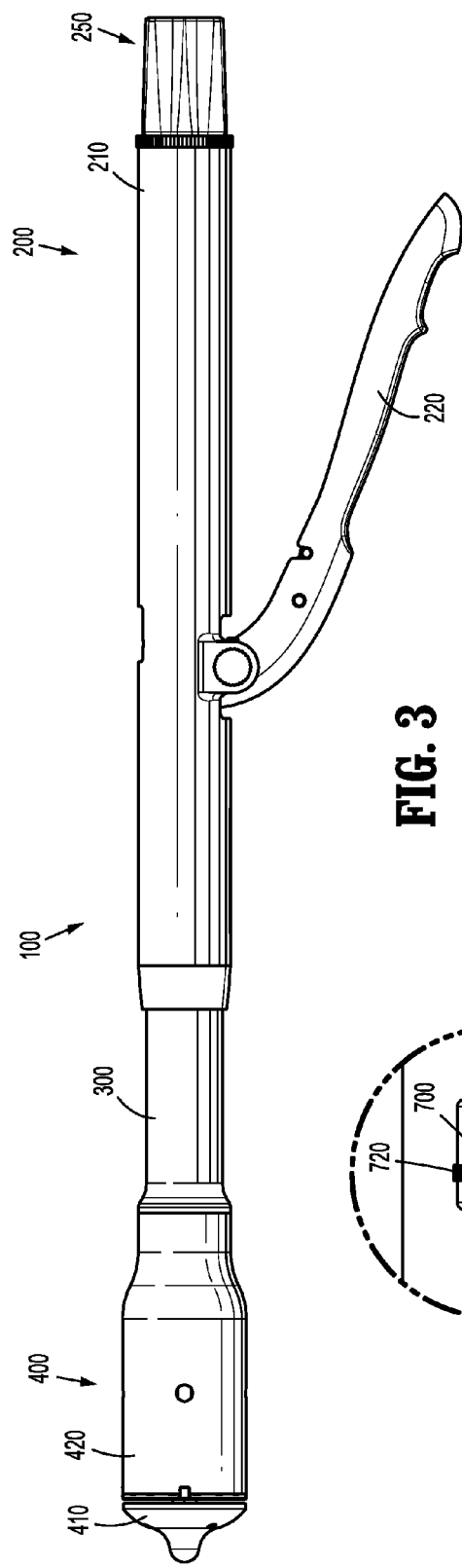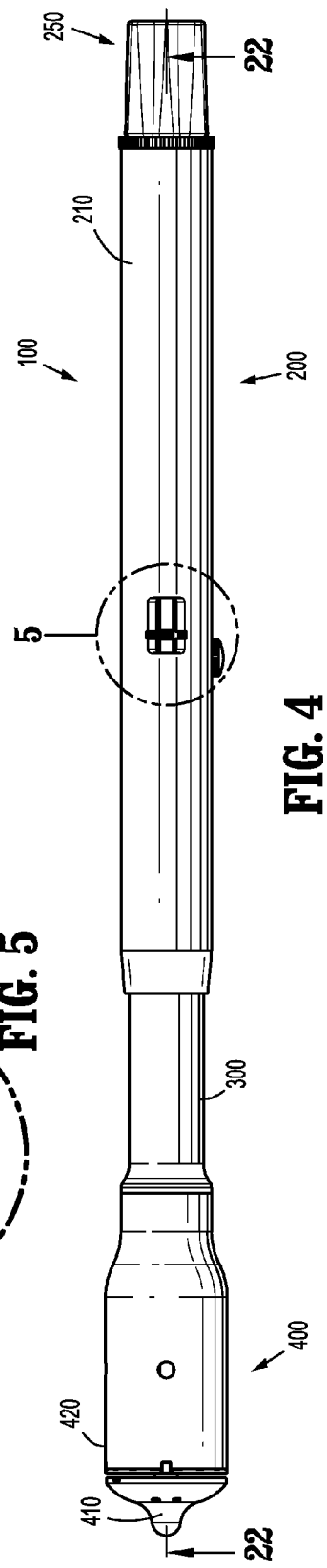
FIG. 3
FIG. 5
FIG. 4

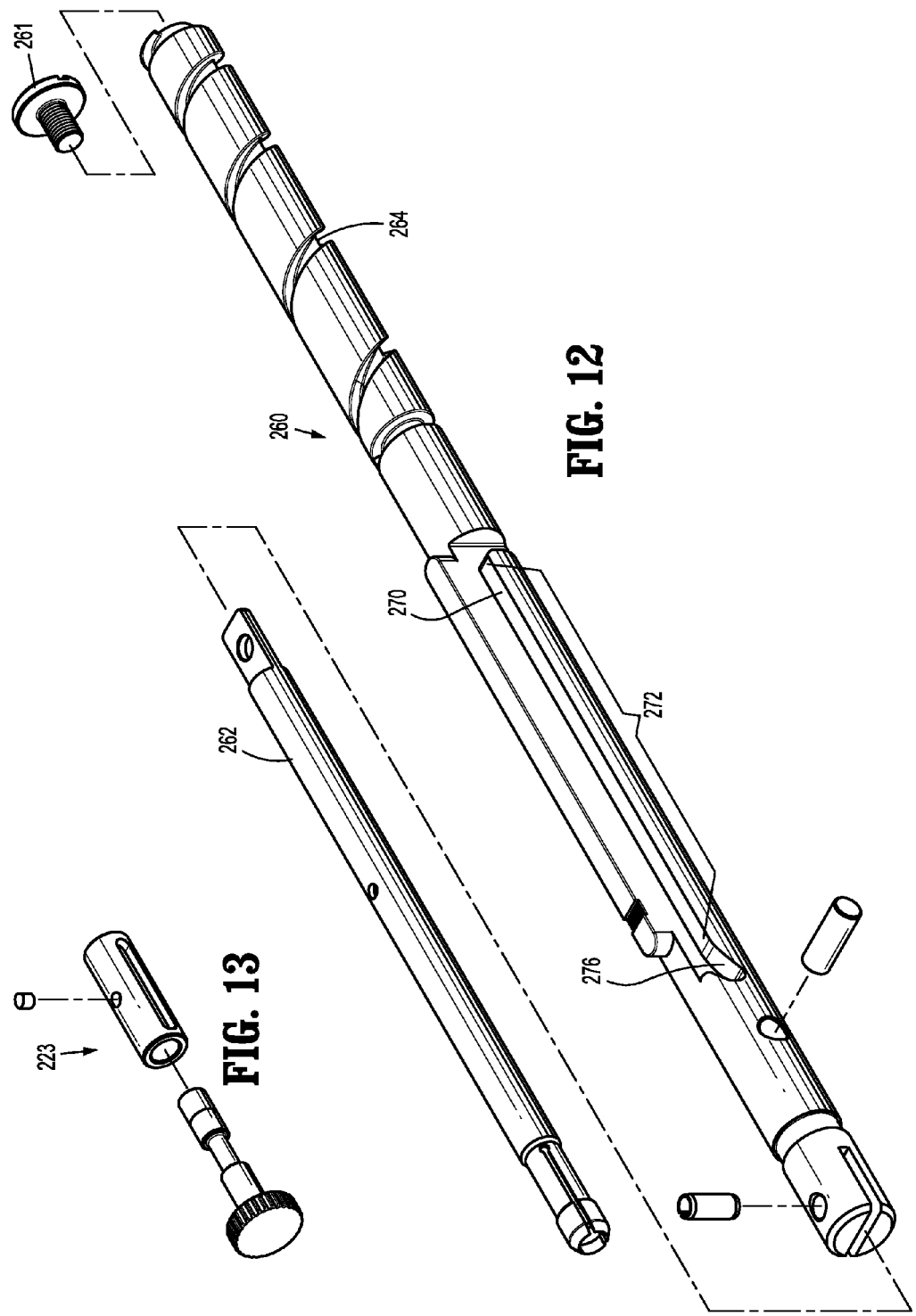

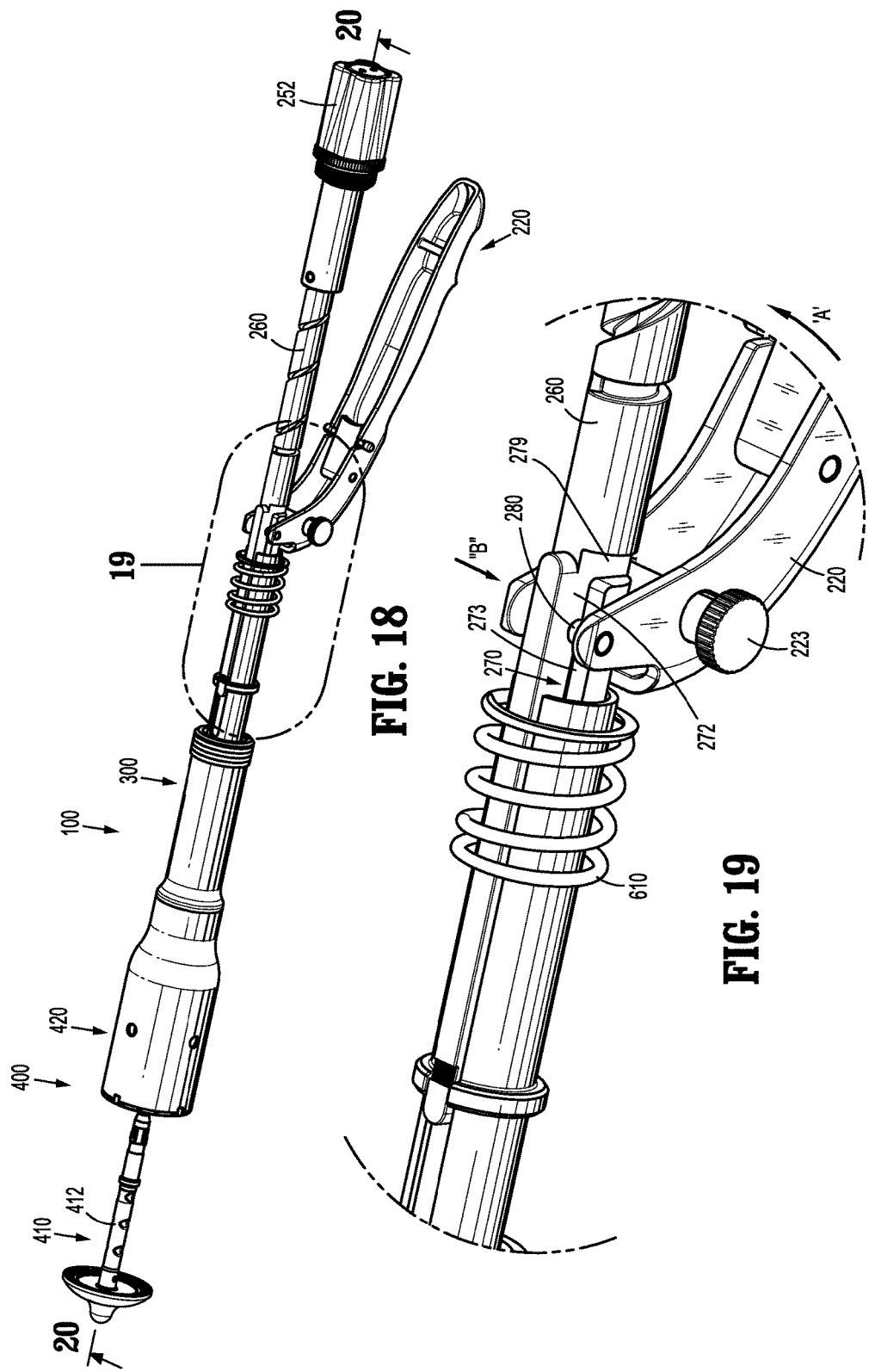

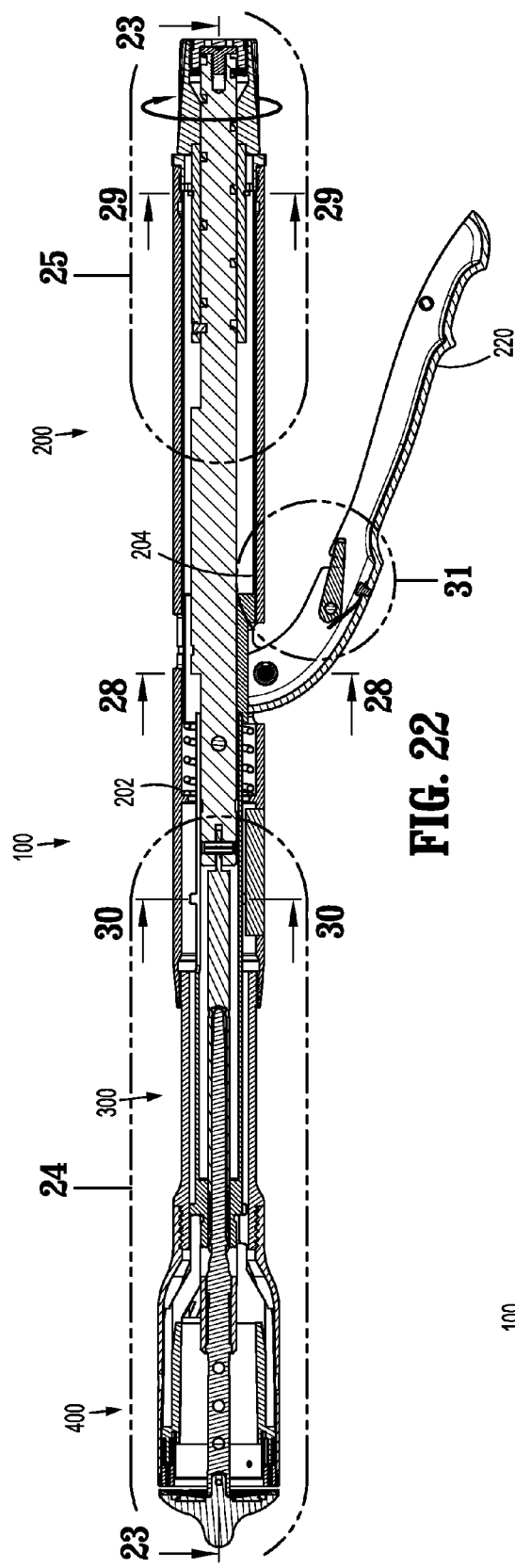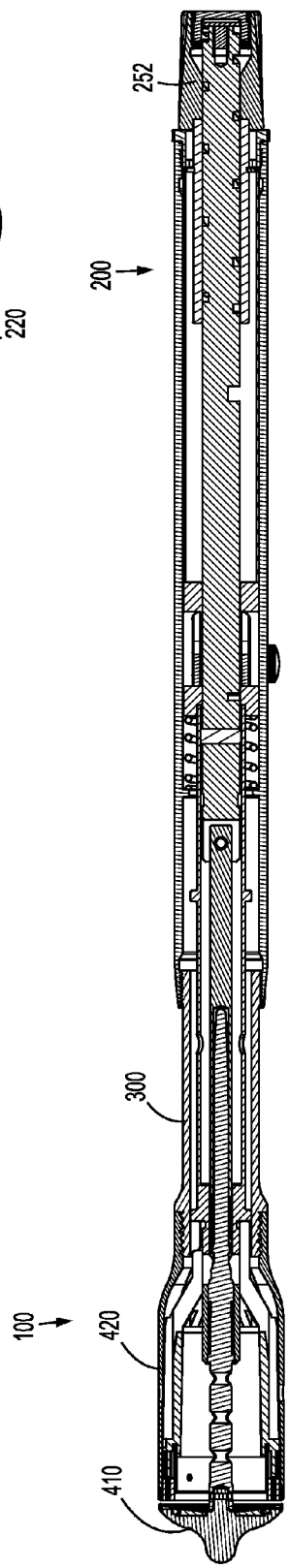
FIG. 22
FIG. 23

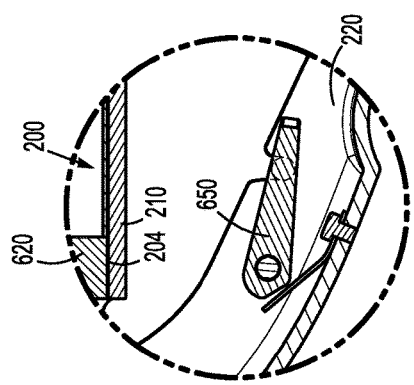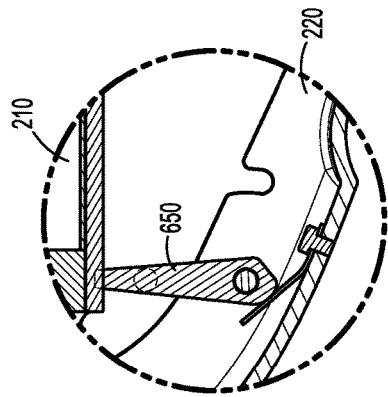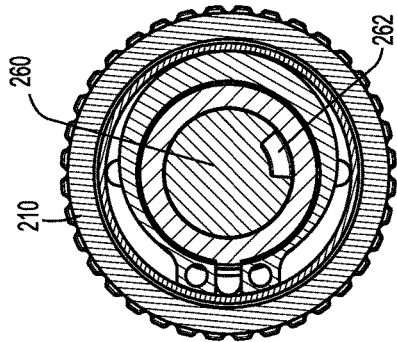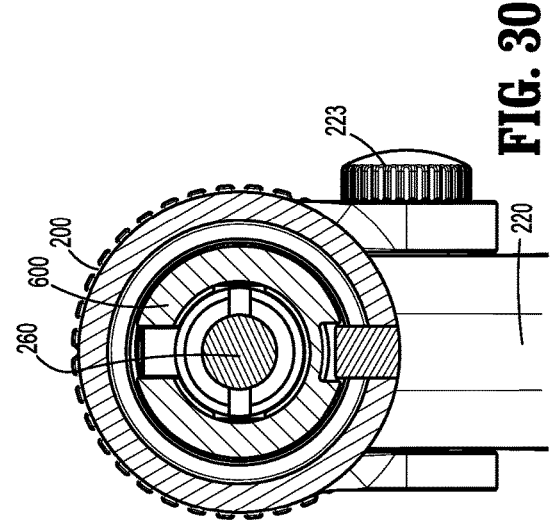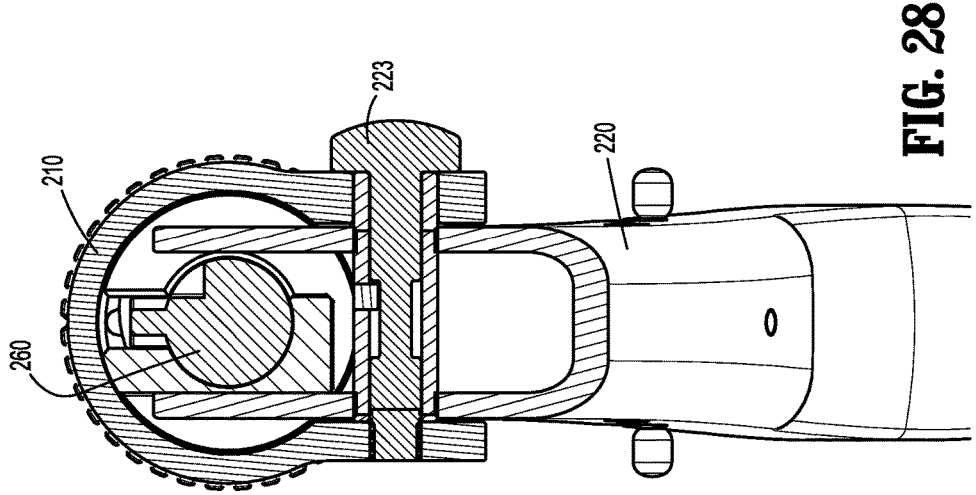

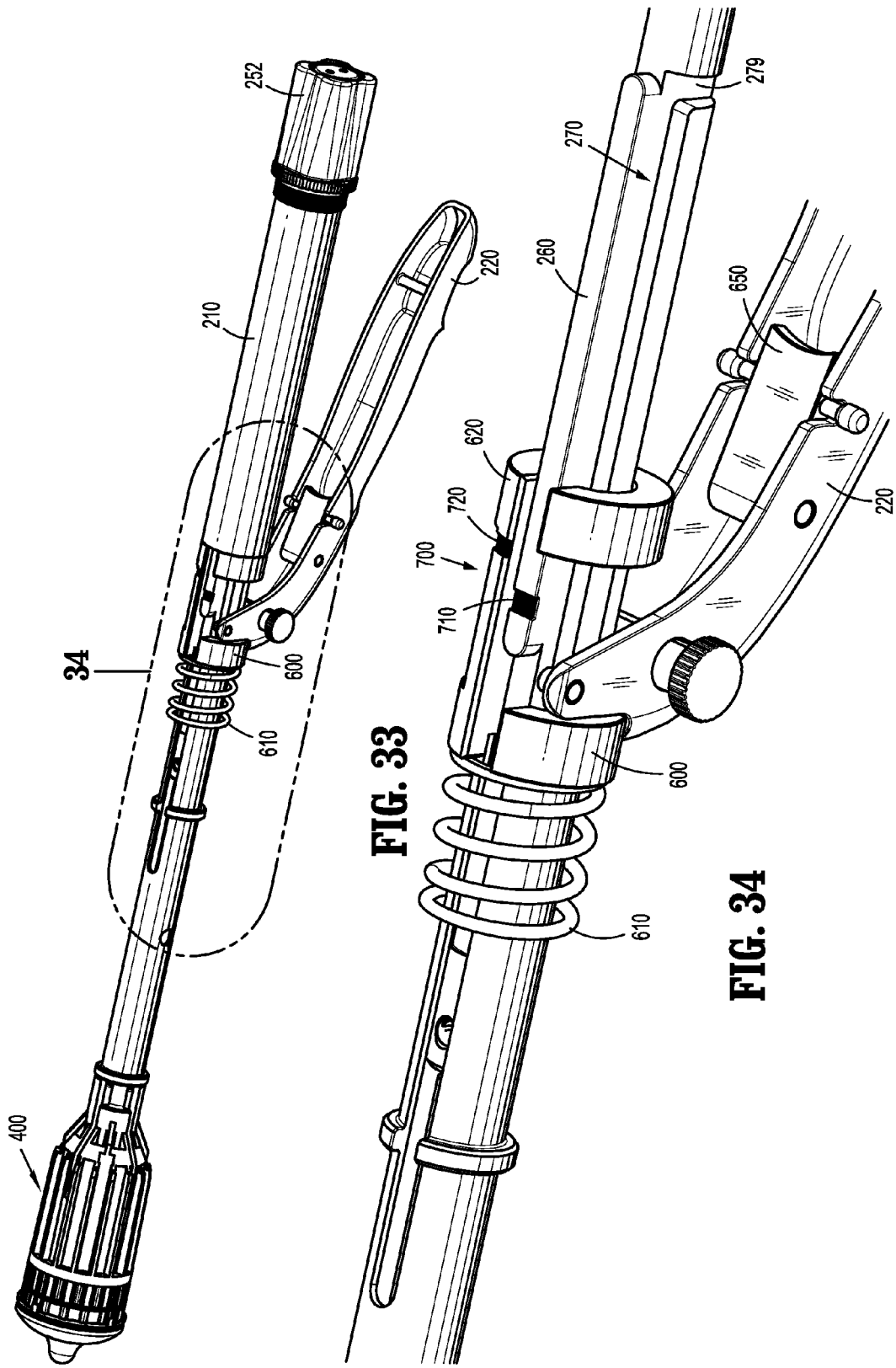

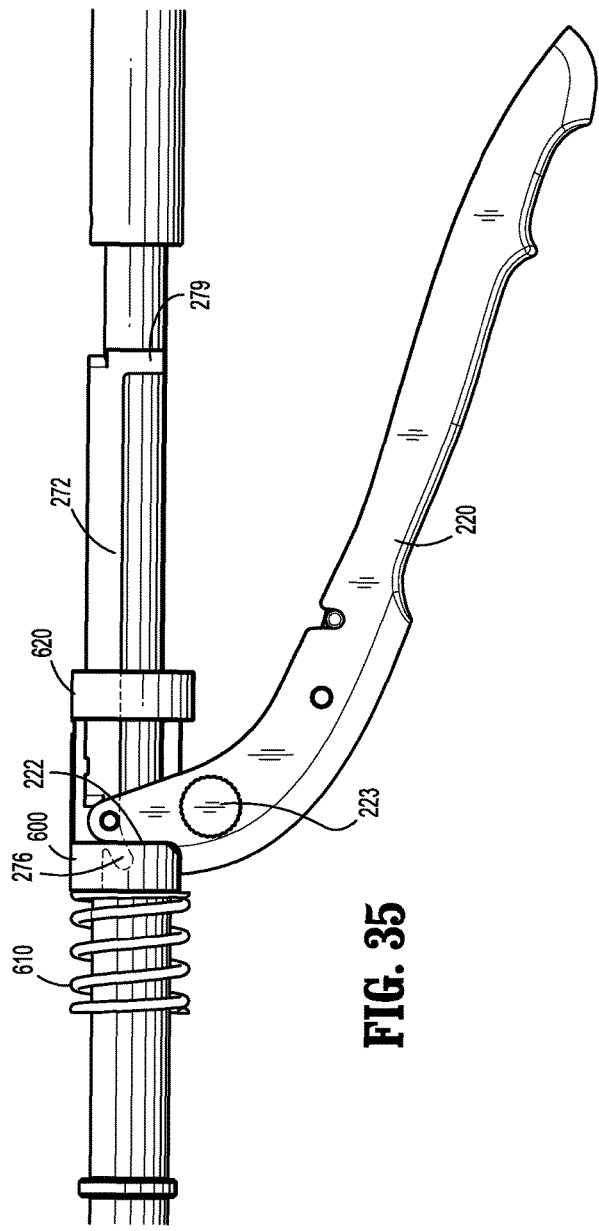
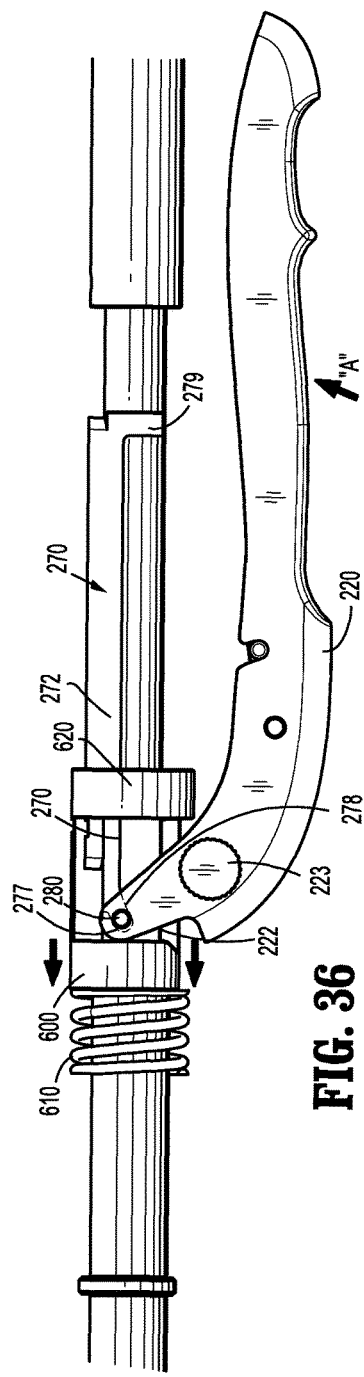
FIG. 35
FIG. 36

SURGICAL INSTRUMENT WITH LOCKOUT MECHANISM

CROSS-REFERENCE TO RELATED APPLICATIONS

This application is a National Stage Application of PCT/CN2013/077331, filed Jun. 17, 2013, under § 371 (a), the entire disclosure of which is incorporated by reference herein.

BACKGROUND

Technical Field

The present disclosure relates generally to a surgical fastening instrument for applying surgical fasteners to body tissue. More particularly, the present disclosure relates to a surgical fastening instrument that is locked out from firing fasteners until the cartridge assembly and anvil assembly are sufficiently approximated.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples or fasteners through the end section of each organ section and simultaneously cores any tissue interior of the driven circular array of staples to free the tubular passage. Examples of instruments for performing circular anastomosis of hollow organs are described for example in U.S. Pat. Nos. 7,303,106, 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with an attached anvil head is mounted to the distal end of the instrument adjacent the staple holding component. Opposed end portions of tissue of the hollow organ(s) to be stapled are clamped between the anvil head and the staple holding component as these components are approximated. The clamped tissue is stapled by actuation of a trigger to drive one or more staples from the staple holding component so that the ends of the staples pass through the tissue and are deformed by the anvil head. An annular knife is concurrently advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling instrument for hemorrhoid treatment, the anvil head and the staple holding component of the surgical stapling instrument are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue and staple the cut tissue. In stapled hemorrhoidopexy, a strip of mucosa and submucosa at the top of the hemorrhoids is removed by the stapling instrument, thereby treating the hemorrhoids by inhibiting blood flow to the tissue.

In certain situations, it is desirable to prevent premature firing of staples. Accordingly, it would be desirable for a surgical instrument to include a lockout mechanism that prevents the movable handle from being actuated until the anvil assembly and the cartridge assembly are sufficiently approximated.

SUMMARY

The present disclosure relates to a surgical instrument comprising a handle assembly, an elongated portion, a head portion, an approximation mechanism, and a lockout mechanism. The handle assembly comprises a movable handle and a stationary handle. The elongated portion extends distally from the handle assembly and defines a longitudinal axis. The head portion is disposed adjacent a distal portion of the elongated portion, and comprises a first jaw member and a second jaw member. The approximation mechanism comprises a drive member disposed in mechanical cooperation with the first jaw member and is configured to longitudinally move the first jaw member in relation to the second jaw member. The lockout mechanism is configured to selectively permit actuation of the movable handle to eject fasteners from the second jaw member. The lockout mechanism comprises a pin extending from the movable handle which is slidingly engaged with a slot in the drive member.

In disclosed embodiments, actuation of the approximation mechanism causes longitudinal translation of the slot with respect to the pin.

In disclosed embodiments, the slot in the drive member includes a blocking portion and a firing portion. When the pin is engaged with the blocking portion of the slot, the movable handle is prevented from being actuated, and when the pin is disposed between the blocking portion and the firing portion of the slot, the movable handle is able to be actuated. Here, it is disclosed that the pin is engaged between the blocking portion and the firing portion of the slot when the first jaw member and the second jaw member are in an approximated position. Here, it is disclosed that the pin is engaged with the firing portion of the slot during actuation of the movable handle. It is further disclosed that the firing portion of the slot is disposed distally adjacent the blocking portion of the slot. It is further disclosed that the blocking portion of the slot is substantially parallel to the longitudinal axis, and the firing portion of the slot is disposed at an angle with respect to the blocking portion of the slot. It is further disclosed that the firing portion of the slot is arcuate.

In disclosed embodiments, the surgical instrument further comprises an approximation knob disposed adjacent a proximal portion of the drive member, and a stopper threadably engaged with a portion of the approximation knob. A blocking portion of the stopper is configured to contact a proximal face of the drive member.

In disclosed embodiments, the handle assembly is threadably engaged with the elongated portion.

The present disclosure also relates to a method of adjusting the minimum tissue gap between a cartridge assembly and an anvil assembly of a surgical instrument. The method comprises providing a surgical instrument comprising a handle assembly, an elongated portion extending distally from the handle assembly and defining a longitudinal axis, a head portion disposed adjacent a distal portion of the elongated portion and comprising a cartridge assembly and an anvil assembly. A tissue-contacting surface of the cartridge assembly and a tissue-contacting surface of the anvil assembly define a tissue gap therebetween. The method also comprises rotating the handle assembly with respect to the elongated portion such that the cartridge assembly moves along the longitudinal axis with respect to the handle assembly, and affixing the handle assembly to the elongated portion to prevent future movement therebetween.

In disclosed embodiments, the elongated portion threadably engages the handle assembly.

In disclosed embodiments, the surgical instrument further comprises an approximation knob disposed in mechanical cooperation with the anvil assembly. Here, the method further comprises rotating the approximation knob to cause longitudinal movement of the anvil assembly with respect to the cartridge assembly. Here, it is disclosed that the surgical instrument further comprises a drive member disposed in mechanical cooperation with the approximation knob and in mechanical cooperation with the anvil assembly, such that rotation of the approximation knob causes longitudinal translation of the drive member and longitudinal translation of the anvil assembly. Here, it is disclosed that the surgical instrument further comprises a stopper threadably engaged with a portion of the approximation knob. It is further disclosed that the method comprises rotating the stopper with respect to the approximation knob until a blocking portion of the stopper contacts a proximal face of the drive member. It is further disclosed that the method comprises affixing the stopper to the approximation knob to prevent future movement therebetween.

DESCRIPTION OF THE DRAWINGS

Various embodiments of the presently disclosed surgical stapling instrument are disclosed herein with reference to the drawings, wherein:

FIGS. 1 and 2 are perspective views of the presently disclosed surgical instrument illustrated in an approximated position, in accordance with an embodiment of the present disclosure;

FIG. 3 is a side view of the surgical instrument of FIGS. 1 and 2;

FIG. 4 is a top view of the surgical instrument of FIGS. 1-3 after the surgical instrument has been fired;

FIG. 5 is an enlarged view of the area indicated in FIG. 4;

FIG. 12 is a perspective, assembly view of a drive assembly of the surgical instrument of the present disclosure;

FIG. 13 is a perspective, assembly view of a pivot member of the surgical instrument of the present disclosure;

FIG. 18 is a perspective view of the surgical instrument of the present disclosure with various parts removed, and illustrating a firing assembly in a locked position;

FIG. 19 is an enlarged view of the area indicated in FIG. 18;

FIG. 22 is a cross-section view of the surgical instrument of the present disclosure taken along line 22-22 in FIG. 4;

FIG. 23 is a cross-section view of the surgical instrument of the present disclosure taken along line 23-23 in FIG. 22;

FIG. 28 is a proximal-looking transverse, cross-sectional view taken along line 28-28 in FIG. 22;

FIG. 29 is a transverse, cross-sectional view taken along line 29-29 in FIG. 22;

FIG. 30 is a proximal-looking transverse, cross-sectional view taken along line 30-30 in FIG. 22;

FIG. 31 is an enlarged view of the area indicated in FIG. 22 illustrating a safety latch in a firing-enabled position;

FIG. 32 illustrates the safety latch of FIG. 31 in a locked position;

FIG. 33 is a perspective view of the surgical instrument of the present disclosure with various parts removed, and illustrating the firing assembly in a firing-enabled position;

FIG. 34 is an enlarged view of the area indicated in FIG. 33;

FIG. 35 is a side view of portions of the surgical instrument of the present disclosure with various parts removed, and illustrating the firing assembly in a firing-enabled position; and FIG. 36 is a side view of portions of the surgical instrument of the present disclosure with various parts removed, and illustrating the firing assembly in an actuated position.

DETAILED DESCRIPTION OF EMBODIMENTS

Figure 6:
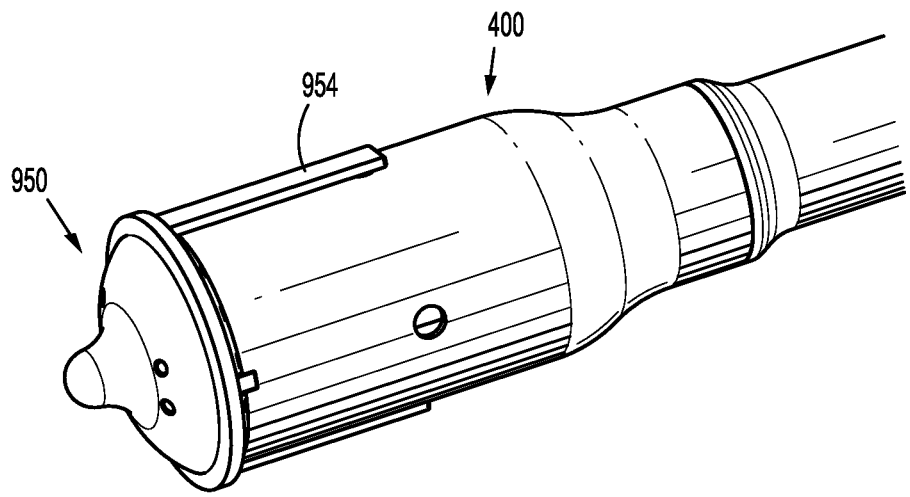
FIG. 6 is a perspective view of a distal end of the surgical instrument of the present disclosure including a shipping wedge thereon.

Embodiments of the presently disclosed surgical instrument will now be described in detail with reference to the drawings in which like reference numerals designate identical or corresponding elements in each of the several views. Throughout this description, the term "proximal" will refer to the portion of the instrument closer to the operator and the term "distal" will refer to the portion of the instrument farther from the operator.

FIGS. 1-36 illustrate an embodiment of the presently disclosed surgical instrument shown generally as 100. Briefly, surgical instrument 100 includes a handle assembly 200, an elongated body portion 300 defining a longitudinal axis X-X, a head portion 400, and a lockout mechanism 500. The length, shape, curvature and/or diameter of elongated body portion 300 and head portion 400 may be varied to suit a particular surgical procedure.

With specific reference to FIGS. 1-4, handle assembly 200 includes a stationary handle 210, a movable handle 220, and an approximation mechanism 250. Head portion 400 includes a first jaw member (i.e., an anvil assembly 410) and a second jaw member (i.e., a shell assembly 420). Anvil assembly 410 is movable in relation to shell assembly 420 between spaced (e.g., FIGS. 18 and 20) and approximated positions (e.g., FIGS. 1, 2 and 22).

Figure 16:
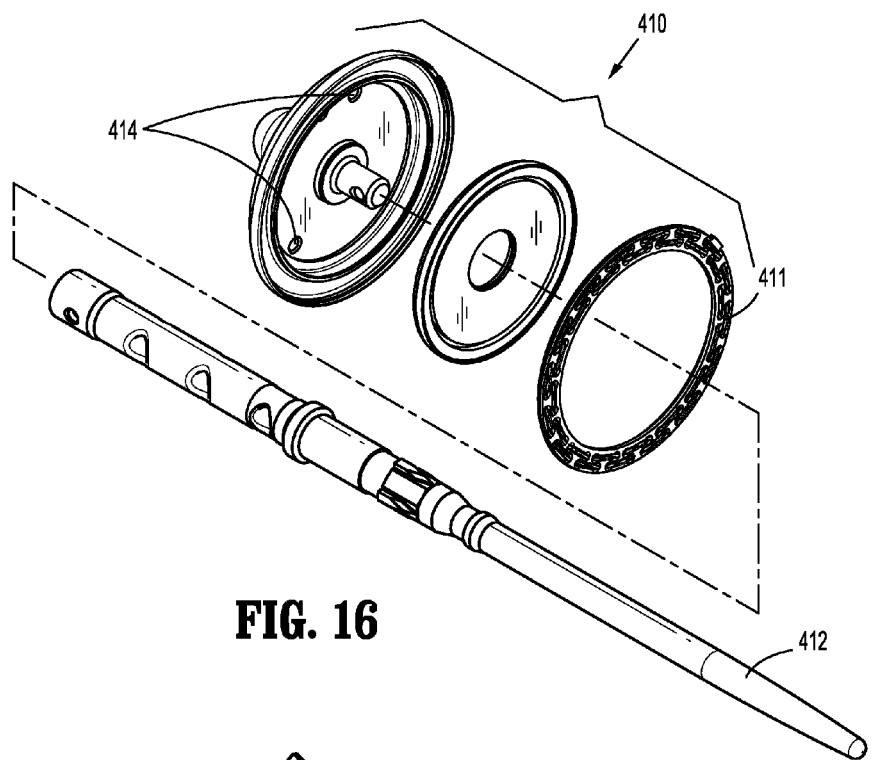
FIG. 16 is a perspective, assembly view of an anvil assembly of the surgical instrument of the present disclosure.
Figure 17:
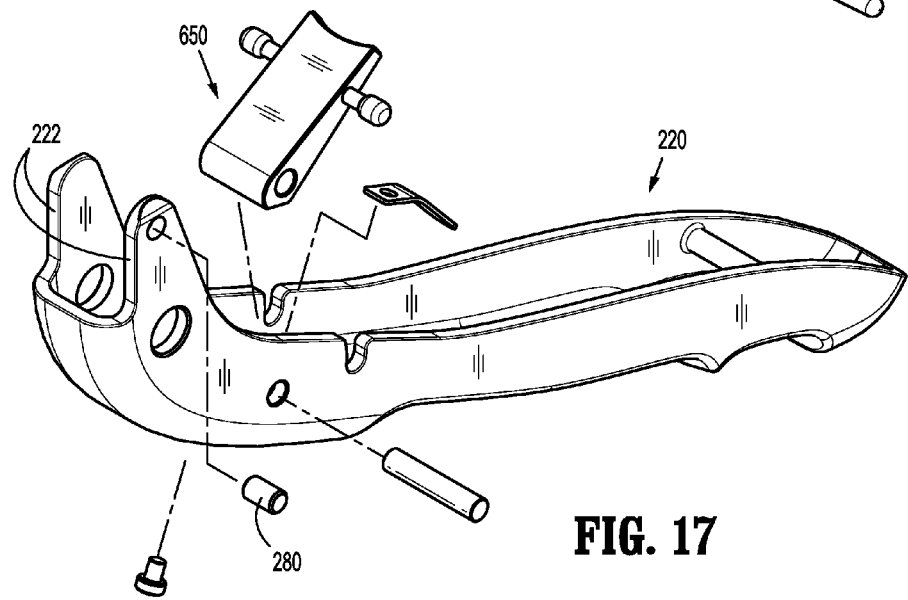
FIG. 17 is a perspective, assembly view of a movable handle of the surgical instrument of the present disclosure.
Figure 20:
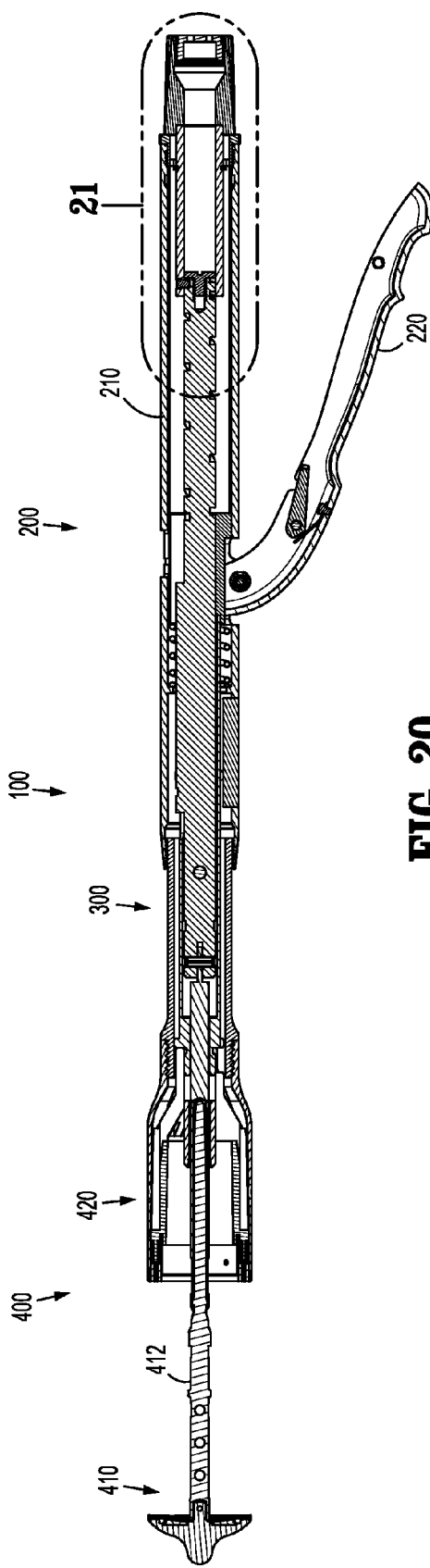
FIG. 20 is a cross-sectional view of the surgical instrument of the present disclosure taken along line 20-20 in FIG. 18.

With reference to FIGS. 9, 12, 15 and 18, further details of approximation mechanism 250 are disclosed. Approximation mechanism 250 includes an approximation knob 252 and a drive member or drive screw 260. Approximation knob 252 is mechanically engaged with drive screw 260, and a distal portion 262 of drive screw 260 is configured to mechanically engage an anvil retainer 412 (FIG. 16). The proximal potion of drive screw 260 includes a helical channel 262 and is slidably positioned within a central bore 253 of a rotatable sleeve 254 (FIG. 15), which extends distally from approximation knob 252. A pin 256 extends through a hole 255 in a distal portion of sleeve 254 into helical channel 264. Sleeve 254 is axially fixed with respect to stationary handle 210. Thus, rotation of approximation knob 252 causes rotation of sleeve 254, which causes pin 256 to move along channel 262 of drive screw 260 to effect axial movement of drive screw 260, and thus a corresponding axial movement of anvil retainer 412 and anvil assembly 410. That is, rotation of approximation knob 252 causes movement of anvil assembly 410 in relation to shell assembly 420 between spaced and approximated positions, More particularly, rotation of approximation knob 252 in a first direction (e.g., clockwise) retracts anvil retainer 412 to cause proximal movement of anvil assembly 410 (i.e., toward shell assembly 420). Rotation of approximation knob 252 in a second opposite direction (e.g., counter-clockwise) distally advances anvil retainer 412 to cause distal movement of anvil assembly 410 (i.e., away from shell assembly 420). Other approximation mechanisms are also contemplated. Further details of the approximation mechanism are described in U.S. Pat. No. 7,303,106, the entire contents of which are incorporated herein by reference.

Referring now to FIGS. 35 and 36, actuation of movable handle 220 (i.e., pivoting in the direction of arrow "A" in FIG. 36), from its firing enabled position (FIG. 35) to its actuated or fired position (FIG. 36), causes fasteners or staples 450 (FIG. 11) to be ejected from shell assembly 420 toward anvil assembly 410. That is, movable handle 220 is disposed in mechanical cooperation with a pusher 600, such that actuation of movable handle 220 causes distal advancement of pusher 600 into direct or indirect contact with staples 450, which causes ejection of staples 450 toward staple deforming pockets 411 (FIG. 16) of anvil assembly 410. More particularly, a biasing element 610 urges pusher 600 proximally into contact with a camming surface 222 of movable handle 220. A distal portion of biasing element 610 is in contact with a wall 202 (FIG. 22) extending radially inwardly from an inner wall 204 of handle assembly 200, thus enabling biasing element 610 to proximally bias pusher 600. When movable handle 220 is actuated, i.e. pivoted about a pivot member 223, camming surface 222 of movable handle 220 is moved distally, camming a proximal portion of pusher 600, which causes distal translation of pusher 600 and ejection of staples 450. Further details of the actuation of the movable handle to cause ejection of staples is described in U.S. Pat. No. 7,303,106, incorporated by reference herein in its entirety.

Referring now to FIGS. 12, 18, 19, 26, 27 and 33-36, lockout mechanism 500 of surgical instrument 100 is shown. Locking mechanism 500 is configured to prevent premature ejection of staples from shell assembly 420. Moreover, locking mechanism 500 prevents actuation of movable handle 220 until anvil assembly 410 has been moved into its approximated position with respect to shell assembly 420. Locking mechanism 500 includes a slot 270 in drive screw 260, and a pin 280 extending from a portion of movable handle 220 and which engages slot 270. With specific reference to FIG. 12, slot 270 includes a first, blocking portion 272, and a second, firing portion 276.

With specific reference to FIG. 19, prior to sufficient approximation of anvil assembly 410, pin 280 of movable handle is within blocking portion 272 of slot 270. In this position, a user is prevented from actuating movable handle 220 in the direction of arrow "A," because an attempt to do so would cause pin 280 to move in the direction of arrow "B" (FIG. 19). As shown, pin 280 is unable to move in the direction of arrow "B" because pin 280 would be forced against a lower wall 273 of blocking portion 272 of slot 270, thus preventing actuation of movable handle 220.

Figure 27:
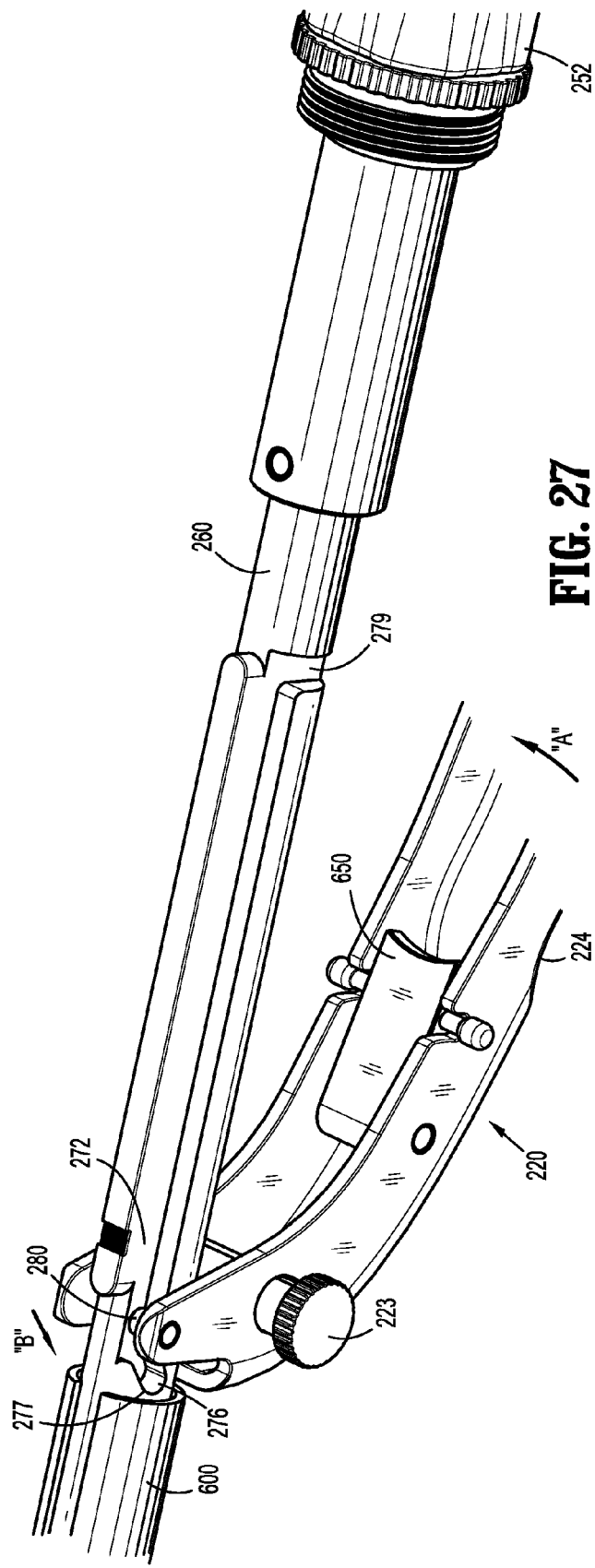
FIG. 27 is an enlarged view of a portion of the surgical instrument illustrated in FIG. 26.

Referring now to FIG. 27, after sufficient approximation of anvil assembly 410, pin 280 of movable handle 220 is adjacent firing portion 276 of slot 270. That is, drive screw 260 has been distally advanced via rotation of approximation knob 252 such that firing portion 276 of slot 270 of drive screw 260 is adjacent pin 280 of movable handle 220. In this position, actuation of movable handle 220 by a user causes a gripping portion 224 of movable handle 220 to move in the direction of arrow "A" and causes pin 280 of movable handle 220 to move in the direction of arrow "B" into firing portion 276 of slot 270. As discussed above, when pin 280 of movable handle 220 moves into firing portion 276 of slot 270, camming surface 222 of movable handle 220 is moved distally, camming a proximal portion of pusher 600, which causes distal translation of pusher 600 and ejection of staples 450.

Additionally, when pin 280 of movable handle 220 is within firing portion 276 of slot 270, drive screw 260 is physically prevented from longitudinal movement. That is, in this position, a user will be prevented from rotating approximation knob 252, as the engagement between pin 280 and firing portion 276 of slot 270 of drive screw 260 would prevent longitudinal movement of drive screw 260. More particularly, the engagement between pin 280 and a distal wall 277 of firing portion 276 of slot 270 would prevent drive screw 260, and thus anvil assembly 410, from proximally translating (see also FIGS. 35 and 36). The engagement between pin 280 and a proximal wall 278 of firing portion 276 of slot 270 would prevent drive screw 260, and thus anvil assembly 410, from distally translating.

After movable handle 220 is actuated to effect firing and the user releases the force against movable handle 220, biasing element 610 urges pusher 600 and thus camming surface 222 of movable handle 220 proximally. Pin 280 is likewise moved proximally out of firing portion 276 of slot 270, thus enabling longitudinal translation of drive screw 260.

Additionally, slot 270 includes a transverse portion 279 disposed at the proximal-most end of slot 270 (FIG. 27). It is envisioned that transverse portion 279 of slot 270 facilitates assembly of surgical instrument 100. That is, during assembly, pin 280 of movable handle 220 is able to enter slot 270 through transverse portion 279.

In the illustrated embodiments, and with particular reference to FIGS. 31 and 32, surgical instrument includes a safety latch 650 disposed in mechanical cooperation with movable handle 220. Safety latch 650 is another feature of surgical instrument 100 that is configured to maintain movable handle 220 in an open, non-actuated position until anvil assembly 410 and shell assembly 420 have been approximated. When safety latch 650 is in the blocking position shown in FIG. 32 (wherein anvil assembly 410 and shell assembly 420 are in an unapproximated (spaced) position), movable handle 220 cannot be squeezed or actuated. When safety latch 650 is in the enabling position shown in FIG. 31 (wherein anvil assembly 410 and shell assembly 420 are in a closed position), movable handle 220 is able to be actuated. It is envisioned that safety latch 650 is biased into its blocking position (FIG. 32), and is movable by a user into its enabling position (FIG. 31). As can be appreciated, safety latch 650 is an additional feature that may be included to help prevent staples from being fired prematurely by physically blocking movement of movable handle 220.

Figure 8:
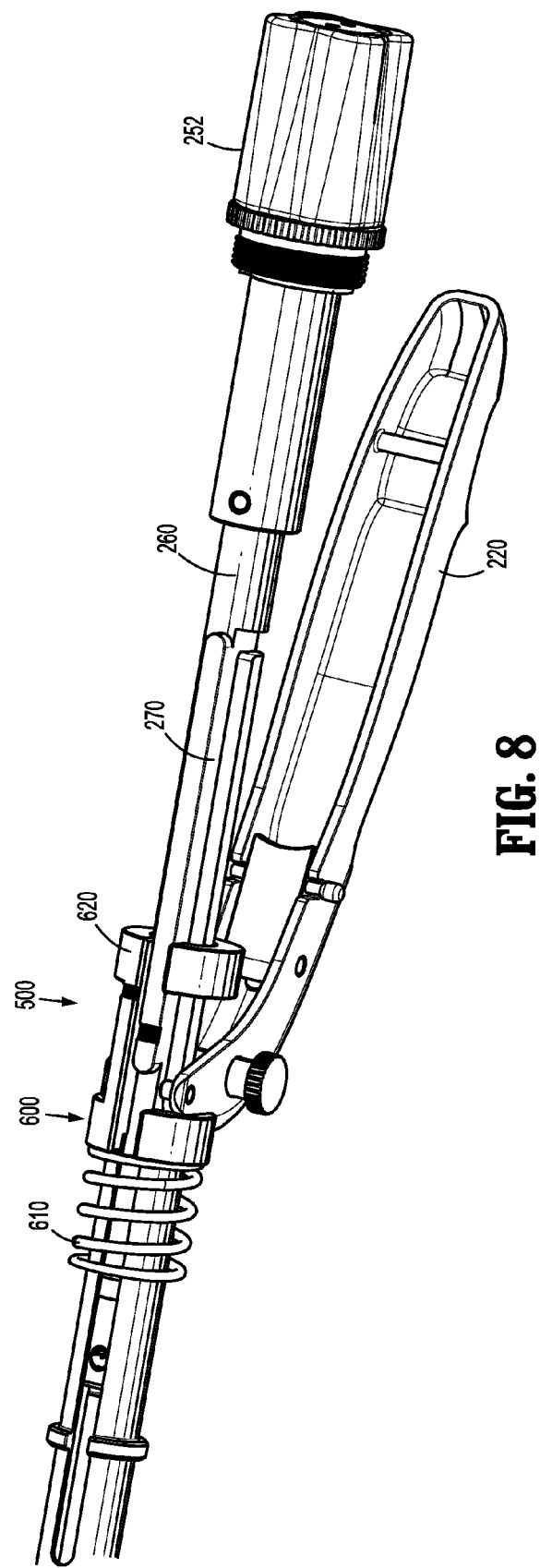
FIG. 8 is a perspective view of a portion of the surgical instrument of the present disclosure with various parts removed.
Figure 9:
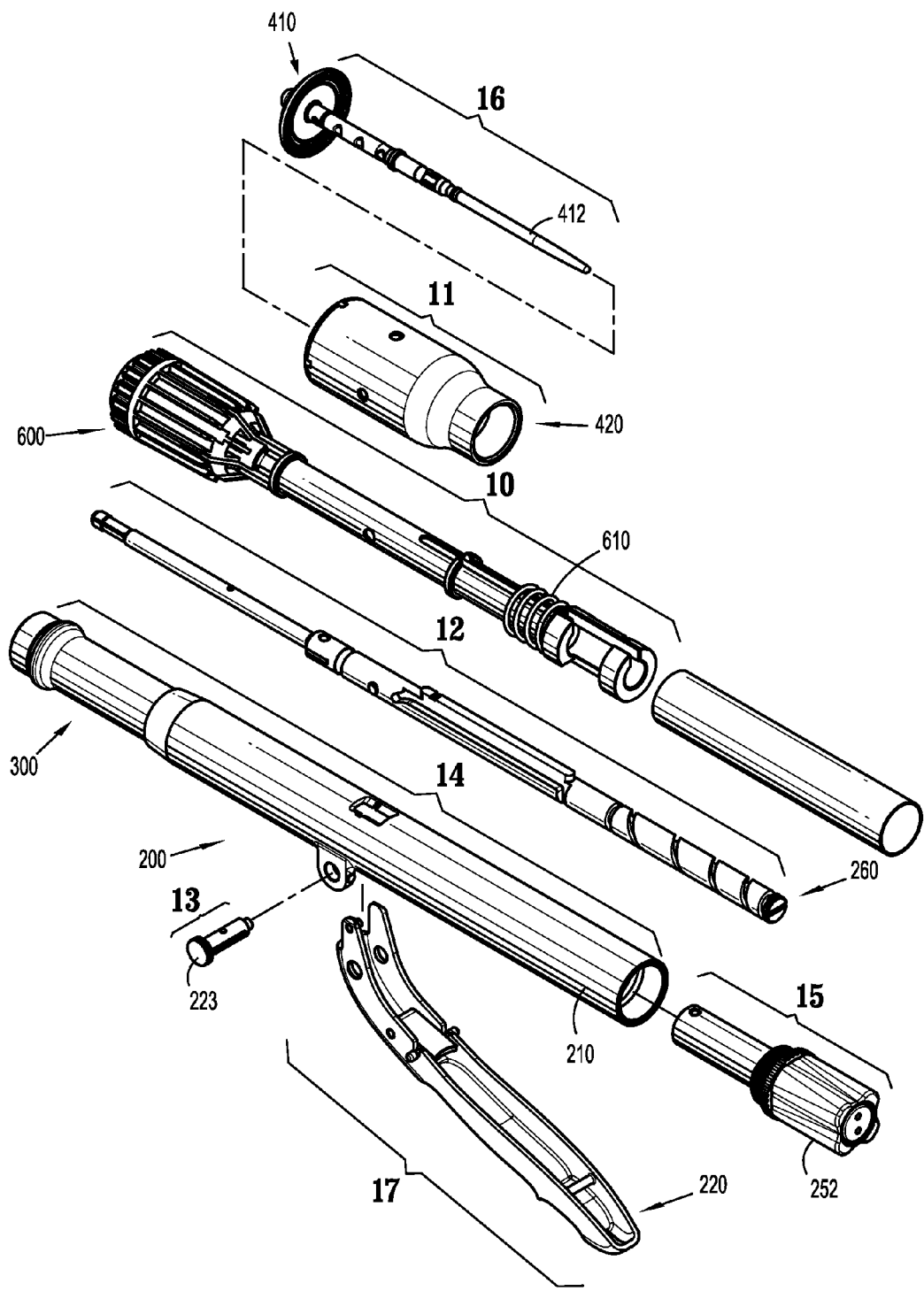
FIG. 9 is a perspective, assembly view of the surgical instrument of the present disclosure.
Figure 10:
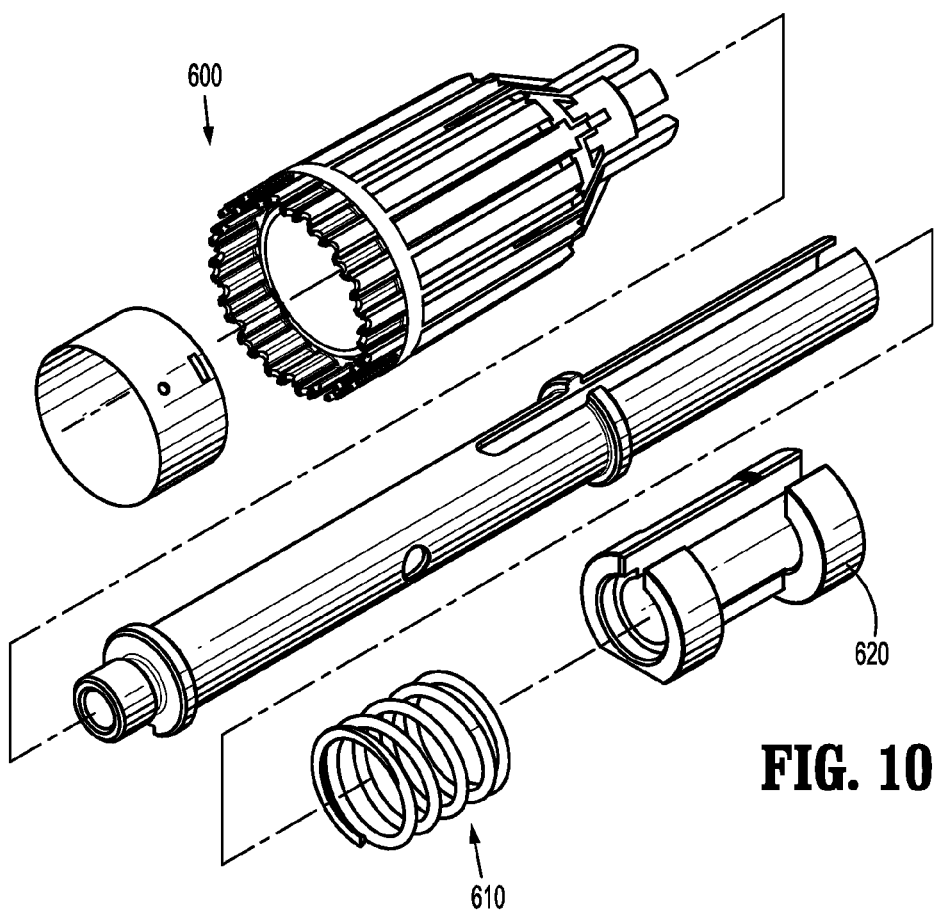
FIG. 10 is a perspective, assembly view of parts of an elongated portion of the surgical instrument of the present disclosure.
Figure 11:
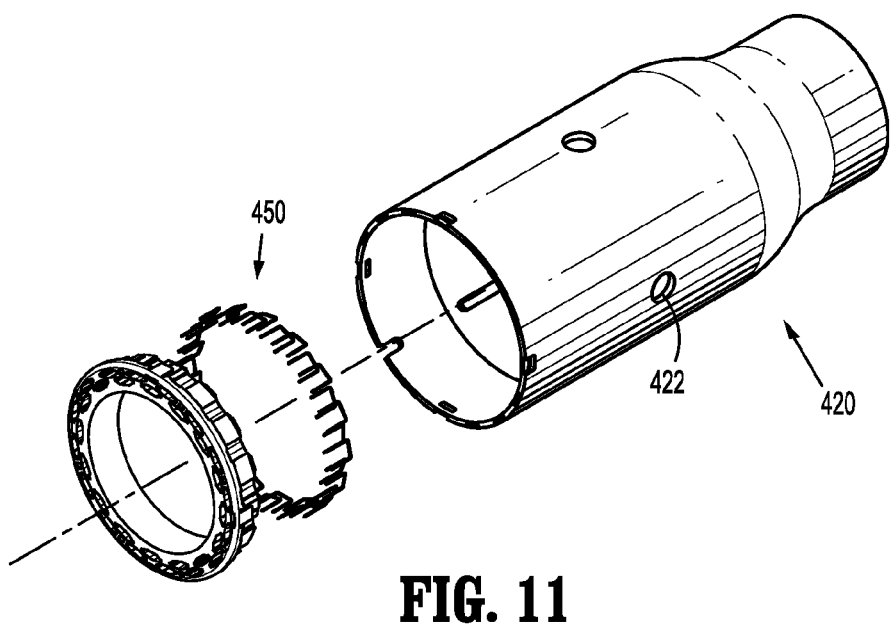
FIG. 11 is a perspective, assembly view of a shell assembly of the surgical instrument of the present disclosure.
Figure 15:
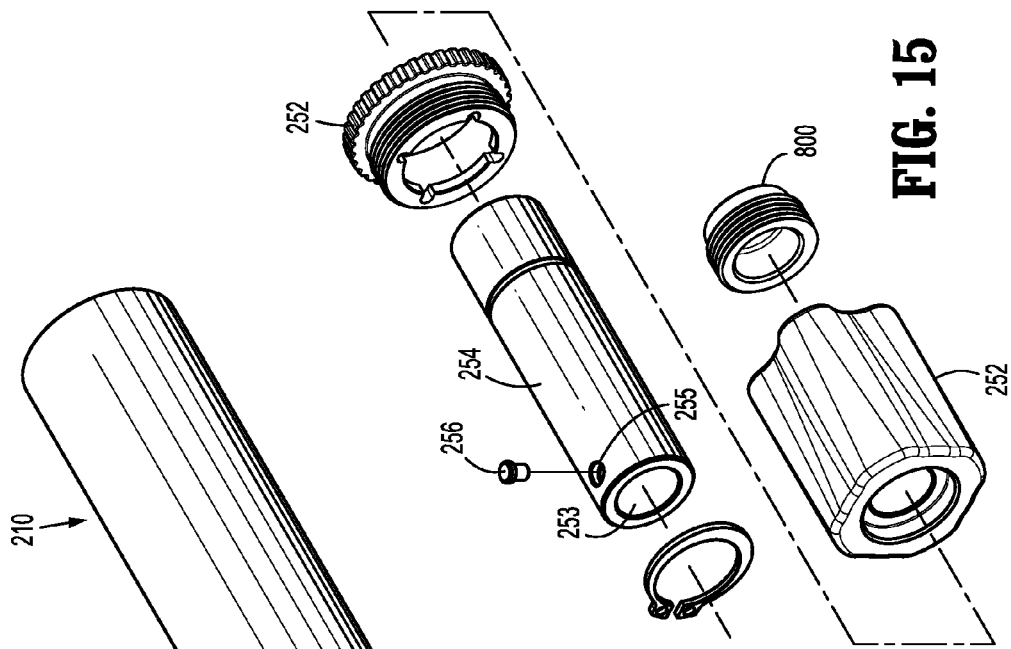
FIG. 15 is a perspective, assembly view of an approximation mechanism of the surgical instrument of the present disclosure.
Figure 14:
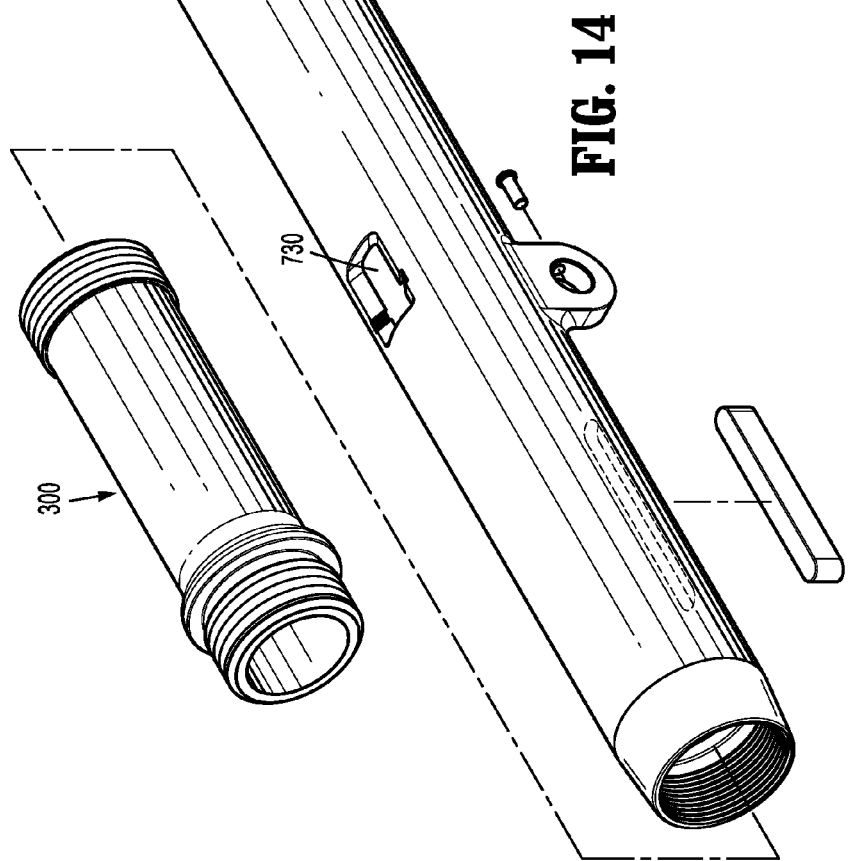
FIG. 14 is a perspective, assembly view of a portion of the handle assembly of the surgical instrument of the present disclosure.

As shown in FIGS. 8 and 10, pusher 600 includes a proximal extension 620. An outer perimeter of at least part of proximal extension 620 contacts an inner wall 204 of handle assembly 200 (see FIGS. 22 and 31). It is envisioned that proximal extension 620 of pusher 600 helps balance the forces enacted on drive screw 260 during firing of surgical instrument 100. That is, the friction between inner wall 204 of handle assembly 200 and proximal extension 620 during longitudinal translation of drive screw 260 helps prevent drive screw 260 from twisting or torquing during firing.

With particular reference to FIGS. 5 and 34, surgical instrument 100 includes an indicator 700. Indicator 700 includes a first indicia 710 disposed adjacent a distal portion of drive screw 260, a second indicia 720 disposed adjacent proximal extension 620 of pusher 600, and a window 730 on handle assembly 200. Indicator 700 is configured to enable a user determine whether staples 450 have been fired from shell assembly 420. A user knows when staples 450 have been fired, when, as viewed through window 730, first indicia 710 is longitudinally aligned with second indicia 720. In FIG. 34, where first indicia 710 and second indicia 720 are longitudinally displaced from each other, movable handle 220 has not yet been actuated and thus no staples have been fired. In FIG. 5, first indicia 710 and second indicia 720 are longitudinally aligned, and thus indicates that surgical instrument 100 has been fired.

Figure 21:
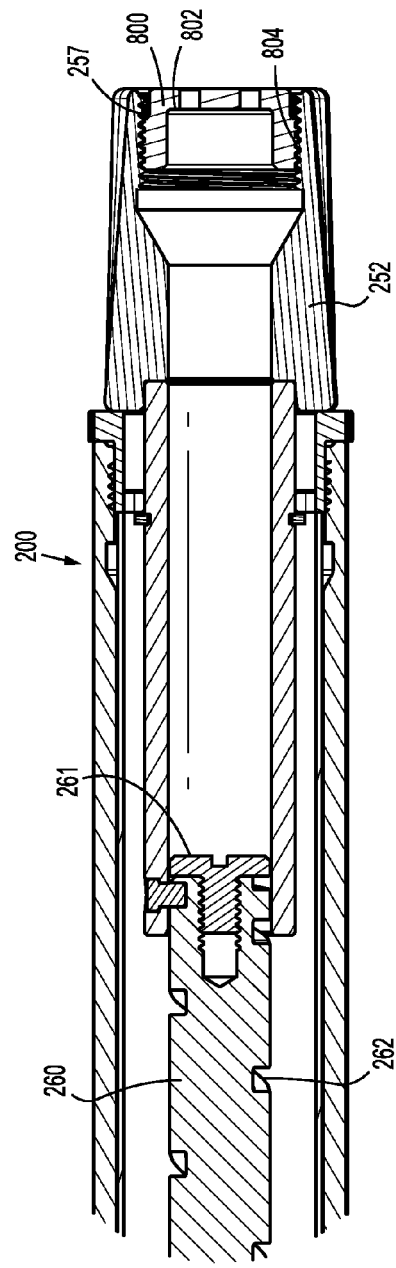
FIG. 21 is an enlarged view of the area indicated in FIG. 20.
Figure 25:
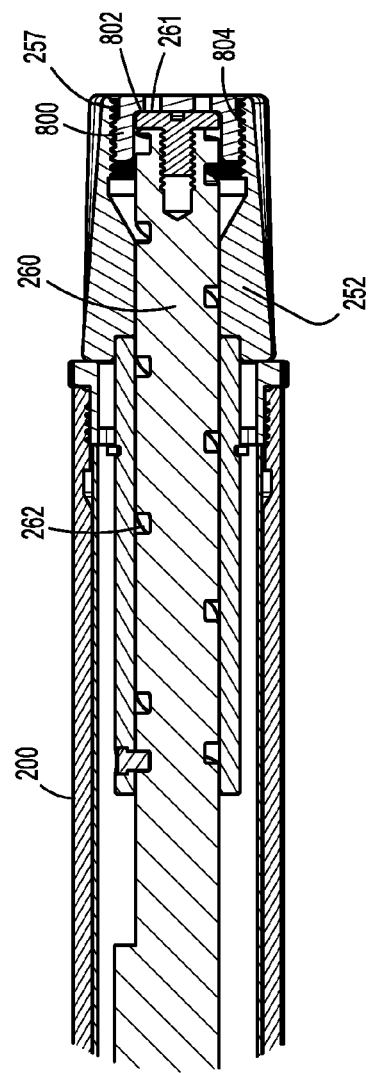
FIG. 25 is an enlarged view of the area indicated in FIG. 22.
Figure 26:
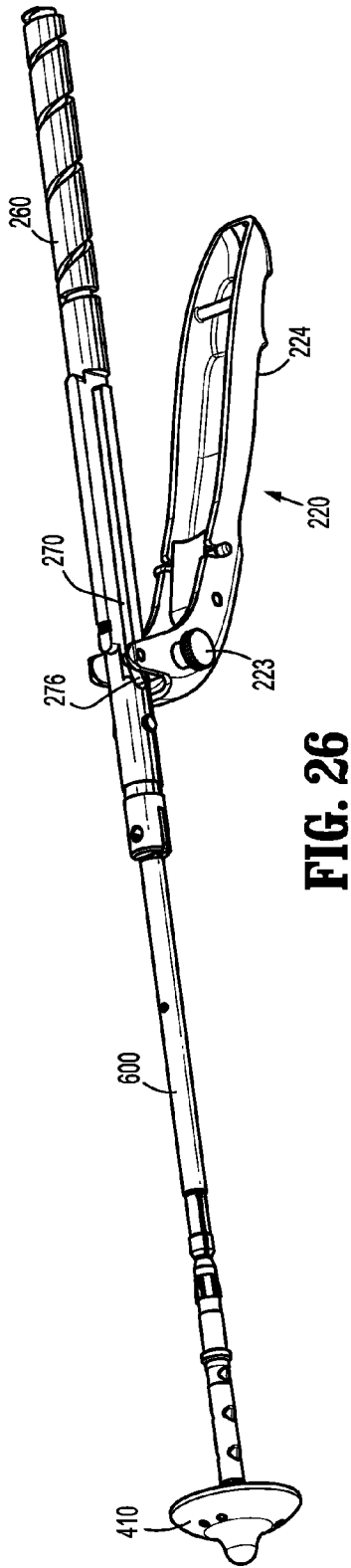
FIG. 26 is a perspective view of the surgical instrument of the present disclosure with various parts removed, and illustrating the firing assembly in a firing-enabled position.

With reference to FIGS. 21 and 25, a stopper 800 is illustrated. Stopper 800 is threadably engaged with approximation knob 252 and is configured to ensure the position of drive screw 260 with respect to pin 280 of movable handle 220. During assembly, approximation knob 252 is rotated a sufficient amount that corresponds to firing position 276 of slot 270 being adjacent pin 280. Once this position is confirmed, stopper 800 is rotated (e.g., advanced distally) until a blocking portion 802 stopper 800 makes contact with a proximal face 261 of drive screw 260 (FIG. 25). Next, during assembly, welding or a thread adhesive, for example, is used where the threads 804 of stopper 800 engage threads 257 of approximation knob 252 to prevent future longitudinal movement of stopper 800 with respect to approximation knob 252. When stopper 800 is in this position and effectively affixed to approximation knob 252, the proper positioning of drive screw 260 (e.g., firing portion 276 of slot 270 therein) with respect to pin 280 is ensured.

Figure 24:
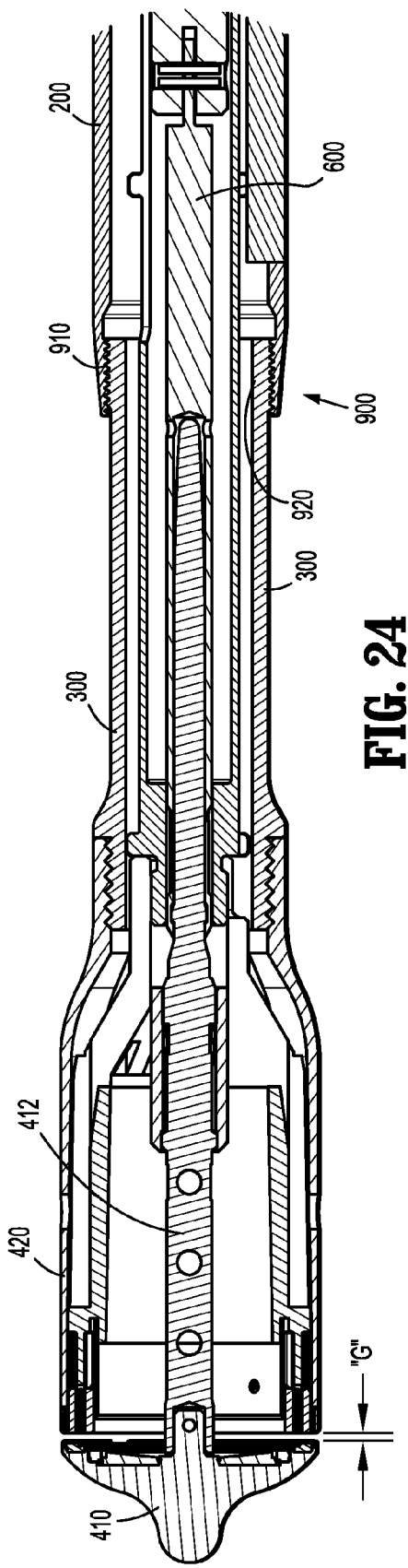
FIG. 24 is an enlarged view of the area indicated in FIG. 22.

Referring now to FIG. 24, surgical instrument 100 includes a tissue gap adjustment mechanism 900. Tissue gap adjustment mechanism 900 enables altering the gap "G" between tissue-contacting surfaces of anvil assembly 410 and shell assembly 420 after assembly of surgical instrument 100. Due in part to the build up of manufacturing tolerances, it is often cost prohibitive to achieve an exact or precise tissue gap "G" in an assembled surgical instrument. In the present disclosure, an exact tissue gap "G" can be achieved without the use of tighter or more strict manufacturing tolerances.

Tissue gap adjustment mechanism 900 includes a first threaded portion 910 disposed adjacent a distal portion of handle assembly 200, and a second threaded portion 920 disposed adjacent a proximal portion of elongated body portion 300. First threaded portion 910 is configured to threadably engage second threaded portion 920. After at least a partial assembly of surgical instrument 100, handle assembly 200 is rotated with respect to elongated body portion 300 to increase or decrease the size of the tissue gap "G" by advancing or retracting shell assembly 420. That is, when handle assembly 200 is rotated in a first direction about the longitudinal axis X-X with respect to elongated body portion 300, shell assembly 420 moves proximally with respect to handle assembly 200 and the tissue gap "G" increases, and when handle assembly 200 is rotated in a second direction about the longitudinal axis X-X with respect to elongated body portion 300, shell assembly 420 moves distally with respect to handle assembly 200 and the tissue gap "G" decreases. Once the desired tissue gap "G" is achieved, welding or a thread adhesive, for example, is used where first threaded portion 910 and second threaded portion 920 are engaged to prevent future longitudinal movement between handle assembly 200 and elongated body portion 300. As can be appreciated, the location of tissue gap adjustment mechanism 900 (i.e., where handle assembly 200 and elongated body portion 300 meet) is not limited to the location shown in the figures, but can be disposed in any reasonable location on surgical instrument 100.

Figure 7:
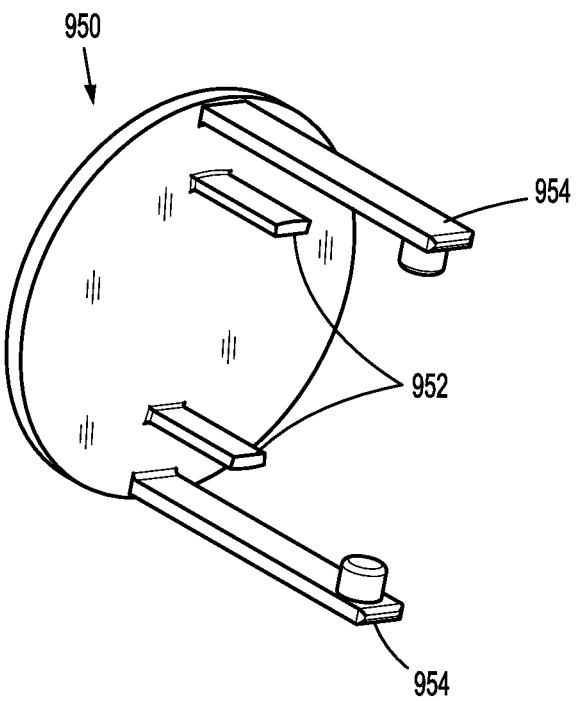
FIG. 7 is a perspective view of the shipping wedge of FIG. 6.

FIGS. 6 and 7 illustrate a shipping wedge 950. Shipping wedge 950 includes a first pair of tines 952 and a second pair of tines 954. Tines 952 are configured to slidingly engage apertures 414 (FIG. 16) on a distal end of anvil assembly 410. Tines 954 are radially-outwardly flexible and are configured to releasably engage openings 422 (FIG. 11) on an outer wall of shell assembly 420. It is envisioned that shipping wedge 950 maintains anvil assembly 410 in a substantially fixed longitudinal position with respect to shell assembly 420 during shipping, storage, etc. of surgical instrument 100.

The present disclosure also relates to a method of performing a surgical procedure using surgical instrument 100 described herein, a method of manufacturing surgical instrument 100 described herein, a method of assembling surgical instrument 100 described herein, and a method of adjusting tissue gap "G" as described herein.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed:

1. A surgical instrument, comprising:
a handle assembly comprising a pivotable handle and a stationary handle;
an elongated portion extending distally from the handle assembly and defining a longitudinal axis;
a head portion disposed adjacent a distal portion of the elongated portion, the head portion comprising a first jaw member and a second jaw member;
an approximation mechanism comprising a drive member disposed in mechanical cooperation with the first jaw member and being configured to longitudinally move the first jaw member in relation to the second jaw member; and
a lockout mechanism configured to selectively permit actuation of the pivotable handle to eject fasteners from the second jaw member, the lockout mechanism comprising a pin extending from the pivotable handle and being slidingly engaged with a slot in the drive member, the slot in the drive member including a blocking portion and a firing portion,
wherein when the pin is engaged with the blocking portion of the slot, the pivotable handle is prevented from being actuated, and when the pin is disposed between the blocking portion and the firing portion of the slot, the pivotable handle is able to be actuated.

2. The surgical instrument of claim 1, wherein actuation of the approximation mechanism causes longitudinal translation of the slot with respect to the pin.

3. The surgical instrument of claim 1, wherein the pin is engaged between the blocking portion and the firing portion of the slot when the first jaw member and the second jaw member are in an approximated position.

4. The surgical instrument of claim 1, wherein the pin is engaged with the firing portion of the slot during actuation of the pivotable handle.

5. The surgical instrument of claim 1, wherein the firing portion of the slot is disposed distally adjacent the blocking portion of the slot.

6. The surgical instrument of claim 1, wherein the blocking portion of the slot is substantially parallel to the longitudinal axis, and wherein the firing portion of the slot is disposed at an angle with respect to the blocking portion of the slot.

7. The surgical instrument of claim 1, wherein the firing portion of the slot is arcuate.

8. The surgical instrument of claim 1, further comprising an approximation knob disposed adjacent a proximal portion of the drive member, further comprising a stopper threadably engaged with a portion of the approximation knob, and wherein a blocking portion of the stopper is configured to contact a proximal face of the drive member.

9. The surgical instrument of claim 1, wherein the handle assembly is threadably engaged with the elongated portion.

10. A surgical instrument, comprising:
a handle assembly comprising a pivotable handle and a stationary handle;
an elongated portion extending distally from the handle assembly and defining a longitudinal axis;
a head portion disposed adjacent a distal portion of the elongated portion, the head portion comprising a first jaw member and a second jaw member;
an approximation mechanism comprising a drive member disposed in mechanical cooperation with the first jaw member and being configured to longitudinally move the first jaw member in relation to the second jaw member; and
a lockout mechanism configured to selectively permit actuation of the pivotable handle to eject fasteners from the second jaw member, the lockout mechanism comprising a pin extending from the pivotable handle and being slidingly engaged with a slot in the drive member, wherein the drive member is prevented from moving in a first direction with the pin in a first position with respect to the slot in the drive member, and the drive member is movable in the first direction with the pin in a second position with respect to the slot in the drive member; and wherein actuation of the approximation mechanism causes longitudinal translation of the slot with respect to the pin.

11. A surgical instrument, comprising:
a handle assembly comprising a pivotable handle and a stationary handle;
an elongated portion extending distally from the handle assembly and defining a longitudinal axis;
a head portion disposed adjacent a distal portion of the elongated portion, the head portion comprising a first jaw member and a second jaw member;
an approximation mechanism comprising a drive member disposed in mechanical cooperation with the first jaw member and being configured to longitudinally move the first jaw member in relation to the second jaw member;
an approximation knob disposed adjacent a proximal portion of the drive member;
a stopper threadably engaged with a portion of the approximation knob, wherein a blocking portion of the stopper is configured to contact a proximal face of the drive member; and
a lockout mechanism configured to selectively permit actuation of the pivotable handle to eject fasteners from the second jaw member, the lockout mechanism comprising a pin extending from the pivotable handle and being slidingly engaged with a slot in the drive member, wherein the drive member is prevented from moving in a first direction with the pin in a first position with respect to the slot in the drive member, and the drive member is movable in the first direction with the pin in a second position with respect to the slot in the drive member.

* * * * *